United States Patent [19]
Simonian et al.

[11] Patent Number: 6,099,530
[45] Date of Patent: Aug. 8, 2000

[54] SOFT-TISSUE INTRA-TUNNEL FIXATION DEVICE

[75] Inventors: Peter T. Simonian, Seattle, Wash.; Russell Warren, Greenwich, Conn.; Deborah N. Adams, Natick; Gene DiPoto, Milford, both of Mass.

[73] Assignee: Smith & Nephew, Inc., Memphis, Tenn.

[21] Appl. No.: 09/057,912

[22] Filed: Apr. 9, 1998

[51] Int. Cl.$^7$ ................................................ A61B 17/84
[52] U.S. Cl. ............................ 606/75; 606/72; 606/151; 623/13
[58] Field of Search ............................... 606/72, 75, 151, 606/232; 623/13

[56] References Cited

U.S. PATENT DOCUMENTS

| | | | |
|---|---|---|---|
| 3,832,931 | 9/1974 | Talan | 85/83 |
| 3,953,896 | 5/1976 | Treace | 3/1 |
| 3,988,783 | 11/1976 | Treace | 3/1 |
| 4,011,602 | 3/1977 | Rybicki | 3/1.9 |
| 4,301,551 | 11/1981 | Dore et al. | 3/1 |
| 4,464,076 | 8/1984 | Leibhard | 403/297 |
| 4,520,511 | 6/1985 | Gianezio et al. | 3/1.913 |
| 4,590,928 | 5/1986 | Hunt et al. | 128/92 D |
| 4,632,100 | 12/1986 | Somers et al. | 128/92 |
| 4,662,886 | 5/1987 | Moorse et al. | 623/13 |
| 4,693,248 | 9/1987 | Failla | 128/334 C |
| 4,711,232 | 12/1987 | Fischer et al. | 128/92 YF |
| 4,711,234 | 12/1987 | Vives et al. | 128/92 YF |
| 4,716,893 | 1/1988 | Fisher et al. | 128/92 YF |
| 4,738,255 | 4/1988 | Goble et al. | 128/92 YF |
| 4,741,330 | 5/1988 | Hayhurst | 128/92 YF |
| 4,744,793 | 5/1988 | Parr et al. | 128/92 YF |
| 4,772,280 | 9/1988 | Goble et al. | 623/13 |
| 4,776,329 | 10/1988 | Treharne | 623/13 |
| 4,778,468 | 10/1988 | Hunt et al. | 128/92 YR |
| 4,790,850 | 12/1988 | Dunn et al. | 623/16 |
| 4,834,752 | 5/1989 | Van Kampen | 623/13 |
| 4,851,005 | 7/1989 | Hunt et al. | 623/13 |
| 4,863,476 | 9/1989 | Sheppard | 623/18 |
| 4,870,957 | 10/1989 | Goble et al. | 623/17 |
| 4,888,022 | 12/1989 | Huebsch . | |
| 4,895,150 | 1/1990 | Isaacson et al. | 623/22 |
| 4,927,421 | 5/1990 | Goble et al. . | |
| 4,960,420 | 10/1990 | Goble et al. | 606/73 |
| 4,997,433 | 3/1991 | Goble et al. | 606/72 |
| 5,037,422 | 8/1991 | Hayhurst et al. | 606/72 |
| 5,108,431 | 4/1992 | Mansat et al. | 623/13 |
| 5,129,902 | 7/1992 | Goble et al. | 606/65 |
| 5,147,362 | 9/1992 | Goble | 606/72 |
| 5,152,790 | 10/1992 | Rosenberg et al. | 623/13 |
| 5,176,682 | 1/1993 | Chow | 606/72 |
| 5,211,647 | 5/1993 | Schmeiding | 606/104 |
| 5,236,445 | 8/1993 | Hayhurst et al. | 606/232 |
| 5,258,016 | 11/1993 | DiPoto et al. | 606/232 |
| 5,268,001 | 12/1993 | Nicholson et al. | 606/72 |
| 5,324,308 | 6/1994 | Pierce | 606/232 |
| 5,632,748 | 5/1997 | Beck, Jr. et al. | 606/89 |

FOREIGN PATENT DOCUMENTS

| | | |
|---|---|---|
| 0 052 573 A1 | 11/1980 | European Pat. Off. . |
| 0 317 406 A1 | 11/1988 | European Pat. Off. . |
| 1082415 | 4/1982 | Russian Federation . |

OTHER PUBLICATIONS

Beck et al., "Anterior Cruciate Ligament Reconstruction with Endoscopic Techniques", pp. 86–98, Operative Technique in Orthopaedics, vol. 2, Apr. 1992.

Innovasive Devices, Inc., ROC Fastener System, Promotional Brochure, date 1994 (or possibly 2/95), two pages.

*Primary Examiner*—Michael Buiz
*Assistant Examiner*—David O. Reip
*Attorney, Agent, or Firm*—Fish & Richardson P.C.

[57] ABSTRACT

A soft tissue fixation device for placement in a bone hole includes a body having an outer surface. A longitudinally extending channel for receiving soft tissue is defined by a portion of the outer surface. The body is constructed to be secured in the bone hole in response to axial motion of the body into the bone hole without requiring further manipulation of the device. The channel is configured to secure soft tissue located within the channel between the portion of the outer surface defining the channel and a wall of the bone hole. A securing member is defined by a second portion of the outer surface for securing the body in the bone hole. A rib located within the channel or a projection configured to be selectively deployed into the channel aid in securing the soft tissue in the channel.

20 Claims, 5 Drawing Sheets

SOFT-TISSUE INTRA-TUNNEL FIXATION DEVICE

BACKGROUND OF THE INVENTION

This invention relates to a soft-tissue intra-tunnel fixation device. Surgical fixation devices are known for securing soft tissue to bone during orthopedic surgical procedures, e.g., in replacement of the anterior cruciate ligament (ACL). The usual procedure is to graft tissue from one part of the body to the site of the injured or degraded ligament. In particular, it is common to graft a portion of the patellar tendon, semi-tendonosis or gracilis graft to the attachment points of a damaged ACL. Synthetic grafts have also been used.

The fixation device secures the graft to the bone until natural healing processes achieve permanent fixation of the graft to the bone. Several approaches have been used to secure the graft both externally on the bone and internally within a bone hole. Staples and interference screws are examples of means employed to achieve fixation.

SUMMARY OF THE INVENTION

According to one aspect of the invention, a soft tissue fixation device for placement in a bone hole includes a body having an outer surface. A longitudinally extending channel for receiving soft tissue is defined by a portion of the outer surface. The body is constructed to be secured in the bone hole in response to axial motion of the body into the bone hole without requiring further manipulation of the device. The channel is configured to secure soft tissue located within the channel between the portion of the outer surface defining the channel and a wall of the bone hole.

Embodiments of this aspect of the invention may include one or more of the following features. A securing member is defined by a second portion of the outer surface for securing the body in the bone hole. The securing member includes a wedge or plurality of wedges configured to oppose motion of the body in a direction tending to remove the body from the bone hole.

In particular embodiments, a rib is located within the channel to aid in securing the soft tissue in the channel. The rib has a rounded edge. A plurality of ribs are located within the channel to aid in securing the soft tissue in the channel. The plurality of ribs decrease in size in a distal direction.

Portions of the outer surface of the body define a plurality of longitudinally extending channels. An end of the body has a longitudinally tapered region. An enlarged region is located at an end of the body of the device. The enlarged region has an opening that is aligned with the longitudinally extending channel. A cannulation extends through the body in an axial direction.

In further embodiments, a projection is configured to be selectively deployed into the channel for further securing the soft tissue in the channel. The body includes a longitudinally extending bore and an inner member is disposable within the bore to deploy the projection.

Portions of the outer surface of the body define a plurality of longitudinally extending channels for receiving soft tissue. Each channel is configured to secure soft tissue located within the channel between the portion of the outer surface defining the channel and the wall of the bone hole. A plurality of projections are configured to be selectively deployed into the channels.

According to another aspect of the invention, a soft tissue fixation device for placement in a bone hole includes a body having an outer surface, a longitudinally extending channel defined by the body, and a projection configured to be selectively deployed into the channel for further securing soft tissue in the channel.

According to another aspect of the invention, a method of securing soft tissue in a bone hole includes positioning soft tissue within a longitudinally extending channel defined by a portion of an outer surface of a fixation device, and inserting the fixation device into the bone hole by axial motion of the fixation device without further manipulation of the device such that the soft tissue is secured between the portion of the outer surface defining the channel and a wall of the bone hole.

Embodiments of this aspect of the invention may include one or more of the following features. A bone hole having a length greater than the overall length of the fixation device is formed in the bone. The step of positioning incudes applying tension to the soft tissue. The soft tissue is secured, e.g., by suturing, over an end of the fixation device. The soft tissue secured over the end of the fixation device is trimmed such that the soft tissue does not protrude from the bone hole.

According to another aspect of the invention, a method of securing soft tissue in a bone hole includes positioning soft tissue within a longitudinally extending channel defined by a portion of an outer surface of a fixation device, inserting the fixation device into the bone hole by axial motion of the fixation device such that the soft tissue is secured between the portion of the outer surface defining the channel and a wall of the bone hole, and deploying a projection into the channel to further secure the soft tissue within the channel.

Among other advantages, the soft tissue fixation device can be used in a variety of surgical applications, e.g., ACL replacement, using a variety of grafts, e.g., patellar tendon, semi-tendonosis, gracilis grafts, or synthetic grafts. The device is inserted with an axial motion only and does not require further manipulation to secure the device in the bone hole, thereby reducing wear on the soft tissue. The soft tissue fixation device and the soft tissue segments reside entirely within the bone hole after the tissue segments are secured around the end of the device and trimmed, which reduces wear on the soft tissue and increases comfort. The projections within the channel facilitate securing the soft tissue segments seated in the longitudinally extending channels. The projections engage the soft tissue segments without cutting the segments.

Other features and advantages of the invention will be apparent from the description of the preferred embodiments, and from the claims.

DESCRIPTION OF THE PREFERRED EMBODIMENTS

Figure 1:
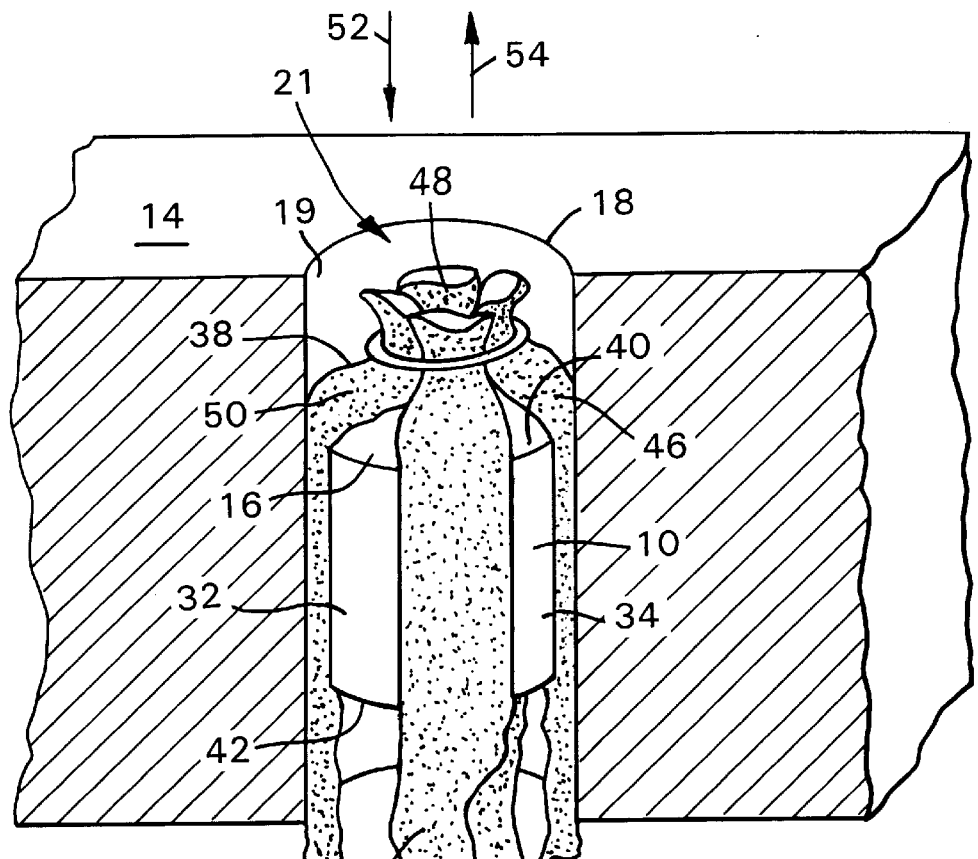
FIG. 1 illustrates a soft-tissue fixation device according to the invention located in a bone hole.
Figure 1:
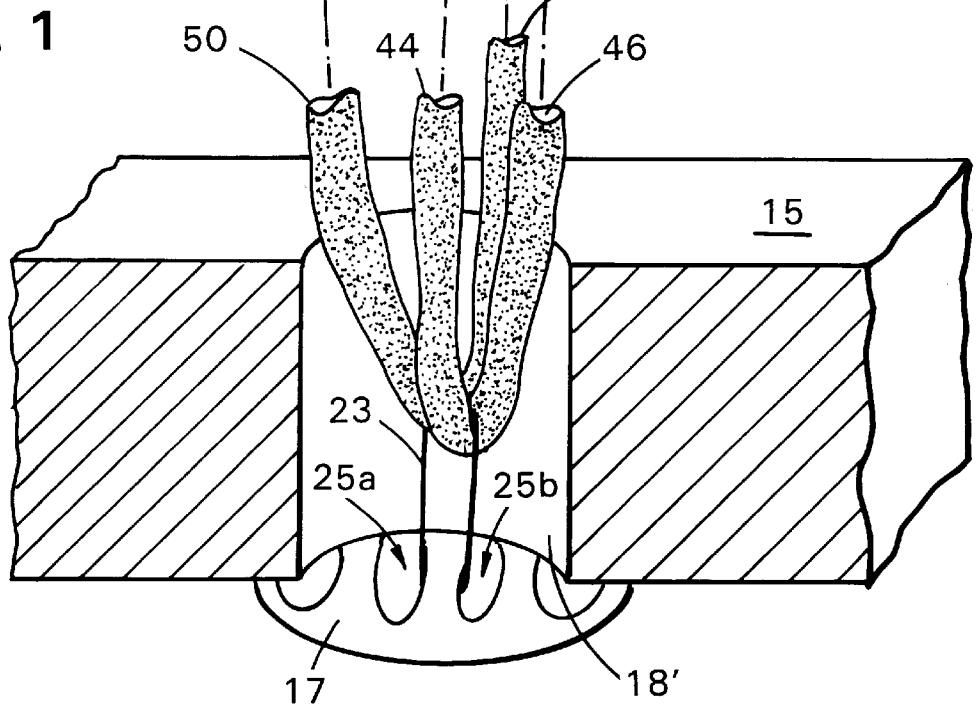

Referring to FIG. 1, a soft tissue fixation device 10 for securing soft tissue 12 to bone 14 includes a device body 16 sized to fit within a bone hole 18. Soft tissue 12 is, e.g., a ligament graft formed from a portion of the patellar tendon, semi-tendonosis or gracilis graft or a synthetic graft. Bone hole 18 is, e.g., a bone tunnel formed in the tibia.

To replace soft tissue such as a damaged ACL, graft 12 is first secured to the femur 15 with a securing device 17, e.g., an endobutton such as described in U.S. Ser. No. 08/795, 847, filed Feb. 5, 1997, titled GRAFT ATTACHMENT DEVICE AND METHOD OF ATTACHMENT, incorporated by reference herein, and U.S. Pat. No. 5,306,301, titled GRAFT ATTACHMENT DEVICE AND METHOD OF USING SAME, incorporated by reference herein. The graft is then secured within bone tunnel 18 in tibia 14 with device 10. Generally, as is known in the art, the endobutton spans across a hole in the femur 15 and graft 12 is attached to endobutton 17 with tape 23 looped through openings 25a, 25b in the endobutton. Graft 12 is then positioned about device body 16, as described below, and device body 16 is inserted into bone tunnel 18 to reside in a region of cancellous tissue.

Figure 2:
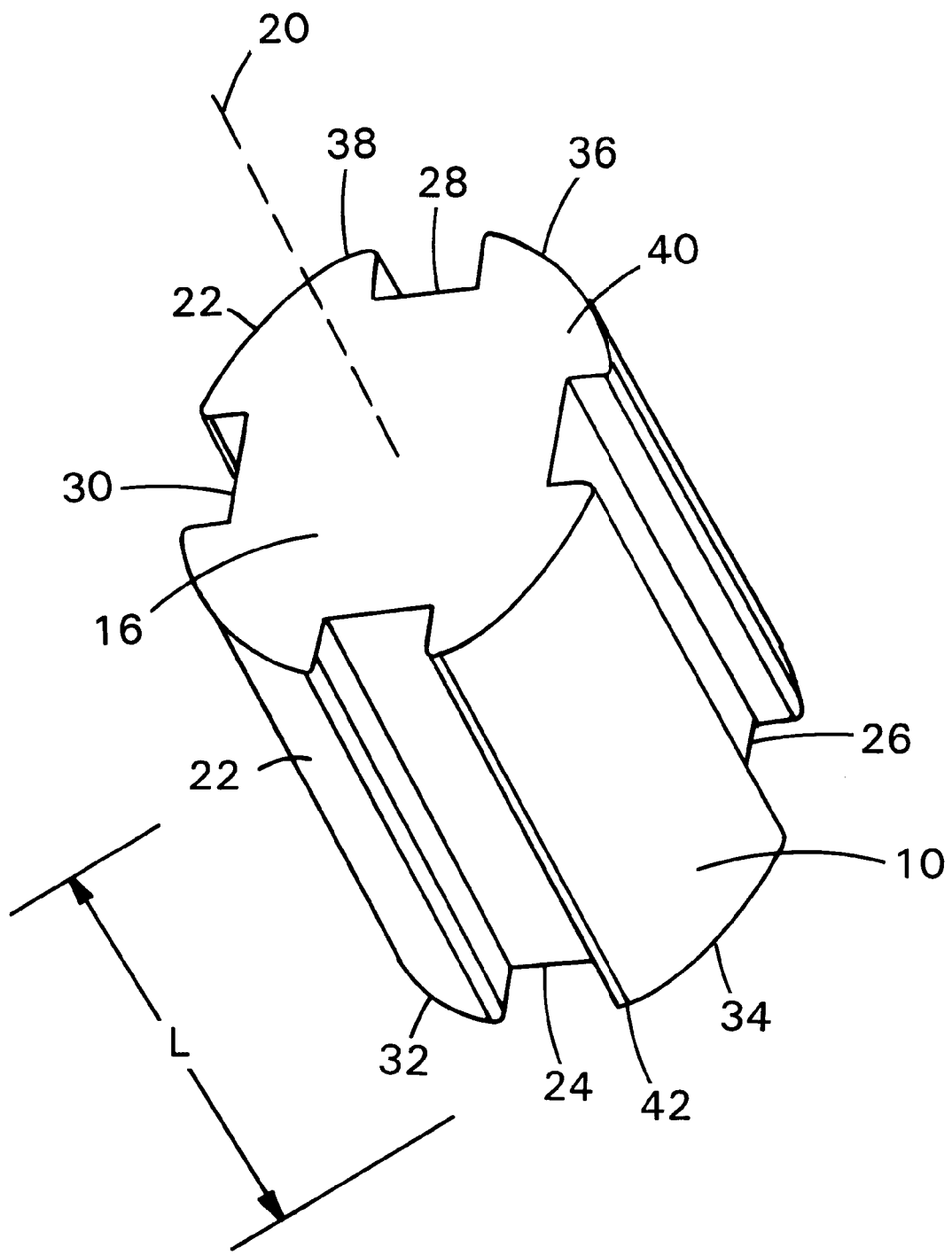
FIG. 2 shows the soft-tissue fixation device of FIG. 1.

Referring also to FIG. 2, device body 16 is generally disposed along a longitudinal axis 20. Device body 16 is generally cylindrical in shape with an outer surface 22 defining longitudinally extending securing members 32, 34, 36, 38, and channels 24, 26, 28, 30 positioned circumferentially between securing members 32, 34, 36, 38. For example, four channels 24, 26, 28, 30 and four securing members 32, 34, 36, 38 are equally spaced about the circumference of device body 16 and extend the entire length, L, of the device body. Ends 40, 42 of device body 16 are flat and are intersected by channels 24, 26, 28, 30.

During use, fixation device 10 is inserted into bone tunnel 18 with soft tissue 12 located within longitudinal channels 24, 26, 28, 30. As shown in FIG. 1, soft tissue 12 includes four tissue segments 44, 46, 48, 50. Each segment is located in one of the four channels. However, the number of tissue segments need not equal the number of channels.

After soft tissue 12 is attached to femur 15, bone tunnel 18 is drilled, and soft tissue 12 is located within channels 24, 26, 28, 30, fixation device 10 is positioned within bone tunnel 18 by applying an axial force to fixation device 10 (along arrow 52) while applying a tensile load to soft tissue 12 (along arrow 54). Fixation device 10 has a larger outer diameter than bone tunnel 18 such that there is an interference fit between securing members 32, 34, 36, 38 and wall 19 of the bone tunnel to secure fixation device 10 to bone tunnel 18. No rotation of fixation device 10 is required to position fixation device 10 within bone tunnel 18. Additionally, there is no need for a second member to be inserted to expand the device or wedge the device in place.

Soft tissue 12 is compressed between the surface of fixation device 10 defining channels 24, 26, 28, 30 and bone wall 19 to secure soft tissue 12 within bone tunnel 18. Soft tissue 12 can be tied off around end 40 of device body 16, e.g., by suturing tissue segments 44, 46, 48, 50 together where the tissue segments exit channels 24, 26, 28, 30. The length, L, of device body 16 is shorter than the length of bone tunnel 18. This configuration allows fixation device 10 and soft tissue 12 to reside completely within bone tunnel 18. Tissue segments 44, 46, 48, 50 can be trimmed after suturing so that they do not extend beyond an opening 21 of bone tunnel 18.

Other embodiments are within the scope of the following claims.

Figure 3:
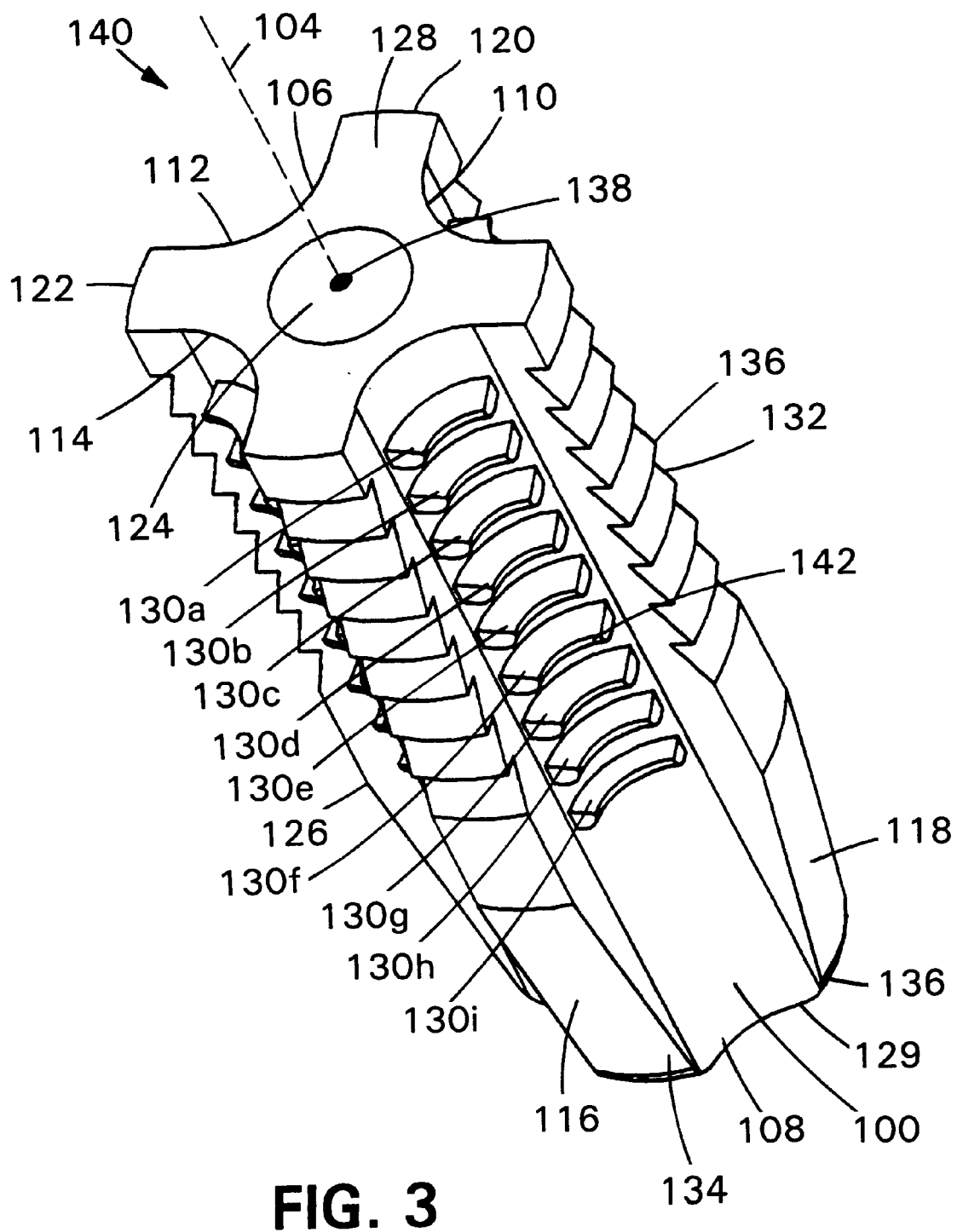
FIG. 3 shows an additional embodiment of a soft-tissue fixation device.

For example, referring to FIG. 3, a soft tissue fixation device 100 has a device body 106 that is generally cylindrical in shape and disposed along a longitudinal axis 104. Device body 106 includes an outer surface 126 that defines four channels 108, 110, 112, 114, and four securing members 116, 118, 120, 122. A proximal end 128 of device body 106 defines a recess 124 for receiving a driver, not shown. A set of ribs, e.g., nine evenly spaced ribs 130a–130i, extend from outer surface 126 into channels 108, 110, 112, 114. The distance that ribs 130a–130i extend from surface 126 generally decreases in the direction of arrow 140 from proximal end 128 toward a distal end 129. For example, ribs 130a–130f project outward 1.28 mm (0.05") from surface 126, rib 130g projects outward 1.21 mm (0.047") from surface 126, rib 130h projects outward 1.00 mm (0.039") from surface 126, and rib 130i projects outward 0.82 mm (0.032") from surface 126. The decrease in distance prevents the ribs 130g, 130h, 130i, which are subject to large forces on insertion, from breaking.

Securing members 116, 118, 120, 122 each include a set of grooves 132 that lie along outer surface 126. Grooves 132 form, e.g., a set of evenly spaced and uniformly sized wedges 136 oriented toward distal end 129 to oppose force applied by soft tissue 12 which would tend to pull fixation device 110 in a distal direction. At a distal section 134, securing members 116, 118, 120, 122 taper to a smaller outer diameter. Distal section 134 is tapered to facilitate insertion of device body 106 into bone tunnel 18.

A cannulation 138 runs through device body 106 for receiving a guidewire (not shown). To aid in inserting fixation device 100 into bone tunnel 18, the guidewire is positioned through bone tunnel 18 and fixation device 100 is passed over the guide-wire and into bone tunnel 18 with the aid of an insertion tool, not shown, located within recess 124. No further manipulation of device 100 is required. For example, neither rotation of the fixation device or insertion of second member to expand the device or wedge the device in place is required to position the fixation device within the bone tunnel.

Ribs 130a–130i engage soft tissue 12 located within channels 108, 110, 112, 114 to aid in securing the soft tissue within the channels and thus within bone tunnel 18. The ribs have rounded tissue contacting edges 142 so that the ribs do not damage the soft tissue.

As discussed above, soft tissue 12 can be tied off around end 128 of device body 106, e.g., by suturing tissue segments 44, 46, 48, 50 together where the tissue segments exit channels 108, 110, 112, 114.

Figure 4:
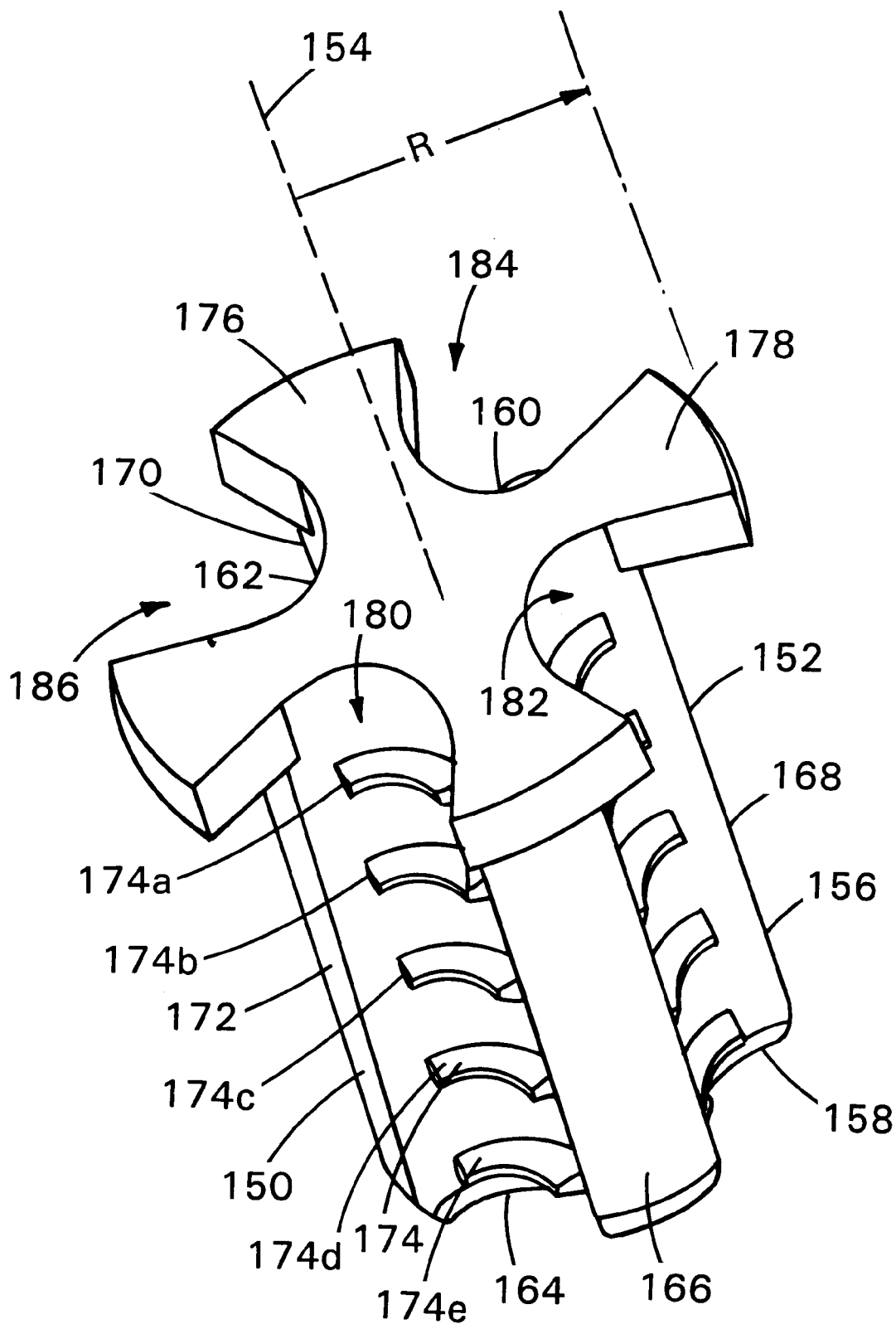
FIG. 4 shows another embodiment of a soft-tissue fixation device.

Referring to FIG. 4, a soft tissue fixation device 150 has a device body 152 that is generally cylindrical in shape and disposed along a longitudinal axis 154. The device body 152 includes an outer surface 156 that defines four channels 158, 160, 162, 164, and four securing members 166, 168, 170, 172. A set of ribs 174a–174e extend from outer surface 156 into channels 158, 160, 162, 164 for securing soft tissue within the channels such that the soft tissue is secured between surface 156 and bone wall 19. Ribs 174a–174e are, e.g., evenly spaced and uniformly sized or tapered as described above with reference to FIG. 3. Device body 152 includes an enlarged head 176 located at a proximal end 178 of device body 152. Enlarged head 176 has a radius, R, larger than the radius of bone tunnel 18. Enlarged head 176 has openings 180, 182, 184, 186 that are aligned with channels 158, 160, 162, 164, respectively, for permitting tissue 12 to pass through head 176.

Fixation device 150 functions similarly to fixation device 10. However, device body 152 is not completely inserted into bone tunnel 18. Enlarged head 176 remains outside bone tunnel 18 and rests against cortical bone while the remainder of device body 152 is inserted into bone tunnel 18. Enlarged head 176 provides additional support for fixation device 150 by resisting forces applied to fixation device 150 by soft tissue 12 which tend to pull the device into the bone hole. After insertion, soft tissue 12 can be connected around enlarged head 176 by, e.g., suturing the segments 44, 46, 48, 50 of the soft tissue 12 where the segments exit the channels 158, 160, 162, 164 through the openings 180, 182, 184, 186.

Figure 6:
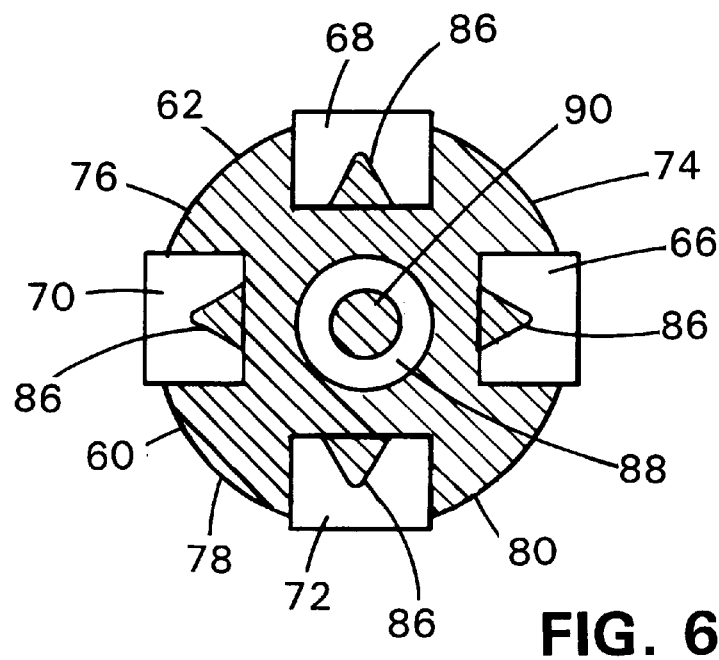
FIG. 6 is an end view of the soft tissue fixation device of FIG. 5.
Figure 5:
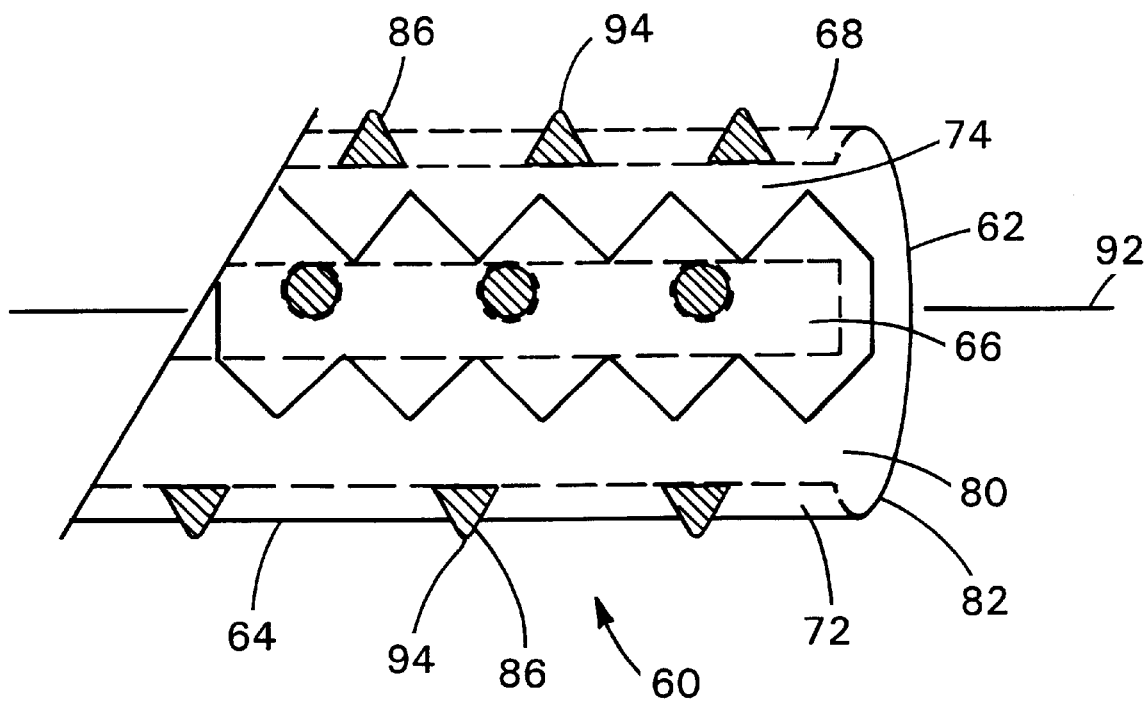
FIG. 5 shows another embodiment of a soft-tissue fixation device.

Referring to FIGS. 5 and 6, a soft tissue fixation device 60 has a device body 62 that is generally cylindrical in shape and disposed along a longitudinal axis 92. Device body 62 includes an outer surface 64 that defines four channels 66, 68, 70, 72, and four securing members 74, 76, 78, 80. Multiple deployable projections 86 are extendable from within device body 62 into channels 66, 68, 70, 72. A central bore 88 extends longitudinally through device body 62. An inner member 90, e.g., a locking screw, can be disposed within bore 88 to engage projections 86 and deploy projections 86 into channels 66, 68, 70, 72.

In operation, fixation device 60 functions similarly to soft tissue fixation device 10, shown in FIGS. 1 and 2. However, projections 86 are deployable and, when deployed, aid in securing secure soft tissue 12 within the channels by engaging the soft tissue. Before projections 86 are deployed, they reside within device body 16. After tissue segments 44, 46, 48, 50, are seated within channels 66, 68, 70, 72, and fixation device 60 is inserted and secured in bone tunnel 18 by applying an axial force to the fixation device, inner member 44 is manipulated, e.g., rotated or inserted, such that projections 86 are engaged. When engaged, projections 86 extend into channels 66, 68, 70, 72 to engage soft tissue 12. Projections 86 have rounded tips 94 so that they do not damage soft tissue 12 when extended.

The various illustrated embodiments of the soft tissue fixation device can be constructed of, e.g., Delrin, acetal, or other non-bioabsorbable or bioabsorbable materials.

Many of the features shown in the embodiments illustrated above can be combined. The tapered distal section 134 of soft tissue fixation device 100 could be combined with the enlarged head 176 of soft tissue fixation device 150. Grooves 132 can be combined with deployable projections or with no projections. Other combinations of the features disclosed are also possible.

What is claimed is:

1. A soft tissue fixation device for placement in a bone hole comprising:

a body having an outer surface, the body being constructed to be secured in the bone hole in response to axial motion of the body into the bone hole without requiring further manipulation of the device, a longitudinally extending channel defined by a portion of the outer surface of the body for receiving soft tissue, the channel being configured to secure soft tissue located within the channel between the portion of the outer surface defining the channel and a wall of the bone hole, and a plurality of ribs located within the channel for securing the soft tissue in the channel, the plurality of ribs decreasing in size in a distal direction.

2. The soft tissue fixation device of claim 1 wherein a second portion of the outer surface of the body defines a securing member for securing the body in the bone hole.

3. The soft tissue fixation device of claim 2 wherein the securing member includes a wedge configured to oppose motion of the body in a direction tending to remove the body from the bone hole.

4. The soft tissue fixation device of claim 2 wherein the securing member includes a plurality of wedges configured to oppose motion of the body in a direction tending to remove the body from the bone hole.

5. The soft tissue fixation device of claim 1 wherein each of the plurality of ribs has a rounded edge.

6. The soft tissue fixation device of claim 1 wherein portions of the outer surface of the body define a plurality of longitudinally extending channels for receiving soft tissue, each channels being configured to secure soft tissue located within the channel between the portion of the outer surface defining the channel and a wall of the bone hole.

7. The soft tissue fixation device of claim 1 further comprising a longitudinally tapered region located at an end of the body.

8. The soft tissue fixation device of claim 1 further comprising an enlarged region located at an end of the body.

9. The soft tissue fixation device of claim 8 wherein the enlarged region defines an opening aligned with the channel.

10. The soft tissue fixation device of claim 1 wherein the body defines a cannulation extending in an axial direction.

11. The soft tissue fixation device of claim 1 wherein the body is sized to form an interference fit with the wall of the bone hole.

12. A soft tissue fixation device for placement in a bone hole comprising:

a body having an outer surface, a longitudinally extending channel defined by a portion of the outer surface of the body for receiving soft tissue, the channel being configured to secure soft tissue located within the channel between the portion of the outer surface defining the channel and a wall of the bone hole, and a projection configured to be selectively deployed into the channel for further securing the soft tissue in the channel.

13. A soft tissue fixation device for placement in a bone hole comprising:

a body having an outer surface, the body being constructed to be secured in the bone hole in response to axial motion of the body into the bone hole without requiring further manipulation of the device, a longitudinally extending channel defined by a portion of the outer surface of the body for receiving soft tissue, the channel being configured to secure soft tissue located within the channel between the portion of the outer surface defining the channel and a wall of the bone hole, and a projection configured to be selectively deployed into the channel for further securing the soft tissue in the channel.

14. The soft tissue fixation device of claim 13, wherein the body includes a longitudinally extending bore, and further comprising an inner member disposable within the bore for deploying the projection.

15. The soft tissue fixation device of claim 13 further comprising a plurality of projections configured to be selectively deployed into the channel.

16. The soft tissue fixation device of claim 13 wherein portions of the outer surface of the body define a plurality of longitudinally extending channels for receiving soft tissue, each channel being configured to secure soft tissue located within the channel between the portion of the outer surface defining the channel and the wall of the bone hole.

17. The soft tissue fixation device of claim 13 further comprising a plurality of projections configured to be selectively deployed into each channel.

18. The soft tissue fixation device of claim 13 wherein a second portion of the outer surface of the body defines a securing member for securing the body in the bone hole.

19. The soft tissue fixation device of claim 18 wherein the securing member includes a wedge configured to oppose motion of the body in a direction tending to remove the body from the bone hole.

20. The soft tissue fixation device of claim 18 wherein the securing member includes a plurality of wedges configured to oppose motion of the body in a direction tending to remove the body from the bone hole.

* * * * *